United States Patent [19]
Grieveson et al.

[11] Patent Number: 5,912,002
[45] Date of Patent: Jun. 15, 1999

[54] CLEANSING COMPOSITION COMPRISING SURFACTANT AND INTERNAL EMULSION COMPRISING COSMETIC AGENT, EMULSIFIER AND CARRIER

[75] Inventors: Ailsa Pauline Grieveson; Margaret Jobling, both of Merseyside, United Kingdom

[73] Assignee: Lever Brothers Company, New York, N.Y.

[21] Appl. No.: 08/653,891

[22] Filed: May 28, 1996

[30] Foreign Application Priority Data

Jun. 13, 1995 [GB] United Kingdom .................. 9511938

[51] Int. Cl.⁶ ....................................... A61K 7/48
[52] U.S. Cl. ...................... 424/401; 424/78.02; 514/846
[58] Field of Search ................. 424/401, 78.02; 514/846

[56] References Cited

U.S. PATENT DOCUMENTS

| | | | |
|---|---|---|---|
| 4,529,605 | 7/1985 | Lynch et al. | 514/552 |
| 5,069,897 | 12/1991 | Orr | 424/66 |
| 5,661,189 | 8/1997 | Grieveson et al. | 514/784 |

FOREIGN PATENT DOCUMENTS

| | | |
|---|---|---|
| 0076146 | 4/1983 | European Pat. Off. . |
| 0152953 | 8/1985 | European Pat. Off. . |
| 0194097 | 9/1986 | European Pat. Off. . |
| 0255364 | 2/1988 | European Pat. Off. . |
| 0281394 | 9/1988 | European Pat. Off. . |
| 0313305 | 4/1989 | European Pat. Off. . |
| 0386898 | 9/1990 | European Pat. Off. . |
| 0391124 | 10/1990 | European Pat. Off. . |
| 0432951 | 6/1991 | European Pat. Off. . |
| 0490749 | 6/1992 | European Pat. Off. . |
| 0514934 | 11/1992 | European Pat. Off. . |
| 0552024 | 7/1993 | European Pat. Off. . |
| 0614660 | 9/1994 | European Pat. Off. . |
| 0616799 | 9/1994 | European Pat. Off. . |
| 0715842 | 6/1996 | European Pat. Off. . |
| 0717978 | 6/1996 | European Pat. Off. . |
| 2162463 | 7/1973 | France . |
| 7405234 | 2/1974 | France . |
| 2280644 | 6/1974 | France . |
| 2258165 | 8/1975 | France . |
| 2693466 | 1/1994 | France . |
| 32 34 365 | 3/1984 | Germany . |
| 2155337 | 9/1985 | United Kingdom . |

*Primary Examiner*—Jyothsna Venkat
*Attorney, Agent, or Firm*—Ronald A. Koatz

[57] ABSTRACT

A rinse-off cleansing composition including at least one surfactant-soluble cosmetic benefit agent and at least one surfactant is provided. The composition comprises a first emulsion having a continuous phase comprising the surfactant and an internal phase comprising a second emulsion. The second emulsion has a continuous phase comprising a carrier in which the cosmetic benefit agent is substantially insoluble and an internal phase comprising the cosmetic benefit agent and an emulsifier therefor. The carrier is surfactant-insoluble. By protecting the cosmetic benefit agent enhanced deposition thereof is achieved during use of the composition.

4 Claims, No Drawings

CLEANSING COMPOSITION COMPRISING SURFACTANT AND INTERNAL EMULSION COMPRISING COSMETIC AGENT, EMULSIFIER AND CARRIER

The present invention relates to a cosmetic composition and, in particular, a rinse-off cleansing composition which contains one or more cosmetic benefit agents which are to be deposited on skin or hair treated therewith.

It is known to include cosmetic benefit agents in cleansing compositions in order to deposit them on skin and/or hair treated therewith. For example, European Patent Specification 386 898 discloses aqueous shampoo compositions comprising anionic surfactant, a water-insoluble sunscreen material and a cationic polymer. The cationic polymer is included to improve deposition of the sunscreen material onto treated hair.

One of the major disadvantages of such compositions to deposit cosmetic benefit agents, particularly "rinse-off" compositions i.e. compositions which are only applied to skin and/or hair temporarily before being removed for example by rinsing or wiping-off, is that effective deposition is not achieved. This is because the benefit agents are often removed from their desired deposition site during the "rinse-off" process. This problem is particularly acute when the beneficial agents are water- and/or surfactant soluble. The problem is generally more pronounced when using compositions to treat skin rather than hair because of the filtering action of hair.

Oil-based compositions in the form of creams, lotions, milks and the like containing oily cosmetic benefit agents, for example sunscreens, intended to be deposited onto skin are known. However, such compositions are typically leave-on, rub-resistant products. Furthermore, they are often water-resistant products and, more importantly, contain little or no surfactant which therefore makes them unsuitable for cleansing skin and hair.

Modification of such known compositions by simply adding surfactant in order to give the cleansing properties is very difficult, if not impossible. Deposition of the cosmetic benefit agent, which is generally surfactant-soluble, from such systems is ineffective since it is solubilised by the surfactant and, therefore, easily carried away from the intended site of deposition as the composition is rinsed off.

In European Patent Specification 552 024 it has been proposed to overcome this problem and provide a rinse-off cleansing composition comprising an emulsion in which effective deposition of the cosmetic benefit agent is achieved by including an additional oil phase in the composition. The cosmetic benefit agent is dissolved in the oil or mixture of oils and thereby protected from the surfactant. The cosmetic benefit agent in the oil forms the internal phase of the emulsion. The surfactant present forms a continuous phase and emulsifies the internal phase.

However, while such a system may result in an improvement in deposition in some instances, the protection provided by the oil is not completely effective since, as the product ages, the distribution of the cosmetic benefit will equilibrate and a proportion equivalent to the relative distribution coefficients will be solubilised into the surfactant and will no longer be available for deposition.

We have now found an improved method of protecting such surfactant sensitive cosmetic benefit agents by trapping them in a carrier droplet. Without being bound by theory, it is believed solublisation of the cosmetic benefit agent is substantially reduced by this route with the result that enhanced deposition of the cosmetic benefit agent is achievable.

Thus, the invention resides in the effective deposition of surfactant solubilised/micellised cosmetic benefit agents from surfactant containing compositions.

Accordingly, the invention provides a rinse-off cleansing composition including at least one surfactant-soluble cosmetic benefit agent and at least one surfactant, the composition comprising a first emulsion having a continuous phase comprising at least one surfactant and an internal phase comprising a second emulsion, the second emulsion having a continuous phase comprising a carrier in which the cosmetic benefit agent is substantially insoluble, said carrier being substantially surfactant-insoluble, and an internal phase comprising the cosmetic benefit agent and an emulsifier for said benefit agent.

An advantage of the composition of the invention is that it provides a means whereby cosmetic benefit agents which are surfactant-soluble can be deposited from surfactant containing compositions. By "surfactant-soluble" it is meant that the cosmetic benefit agent would be solubilisable within micelles of the surfactant in the composition to such an extent that it would be predominantly carried away in the micelles as the composition is rinsed-off treated skin and/or hair.

The present invention also provides a process for preparing a rinse-off cleansing composition as defined above, comprising the steps of:

i) emulsifying the cosmetic benefit agent with an emulsifier in a carrier to form a second emulsion;

ii) adding the second emulsion to a mixture of the at least one surfactant to form a first emulsion; and iii) adding any optional components to the first emulsion.

The present invention also provides a method of depositing a surfactant soluble cosmetic benefit agent from a rinse-off cleansing composition comprising a surfactant, the method comprising providing the cosmetic benefit agent in emulsified form as an internal phase of a second emulsion, the second emulsion having a continuous phase comprising at least one substantially surfactant-insoluble carrier in which the cosmetic agent is substantially insoluble, the second emulsion forming an internal phase of a first emulsion having a continuous phase comprising at least one surfactant.

The present invention further provides the use of an emulsion for depositing a surfactant soluble cosmetic benefit agent from a rinse-off cleansing composition comprising a surfactant, wherein the cosmetic benefit agent is emulsified to form an internal phase of a second emulsion, the second emulsion having a continuous phase comprising at least one substantially surfactant-insoluble carrier in which the cosmetic agent is substantially insoluble, the second emulsion forming an internal phase of a first emulsion having a continuous phase comprising at least one surfactant.

The Cosmetic Benefit Agent

The cosmetic benefit agent may be any surfactant-soluble material (liquid or solid) intended to be deposited onto the hair or skin for the purpose of imparting cosmetic benefits thereto. For example, the cosmetic benefit agent may moisturise, condition and/or protect the skin and/or hair.

Preferred cosmetic benefit agents include:

a) waxes such as carnauba, spermaceti, beeswax, lanolin and derivatives thereof;

b) hydrophobic plant extracts;

c) hydrocarbons such as squalene and squalane;

d) higher fatty acids such as those having at least 12 carbon atoms, for example, lauric, myristic, palmitic, stearic, behenic, oleic, linoleic linolenic, lanolic, isostearic and poly unsaturated fatty acids (PUFA);

e) higher fatty alcohols such as those having at least 12 carbon atoms, for example, lauryl, cetyl, stearyl, oleyl, behenyl, cholesterol and 2-hexadecanol alcohol;
f) esters such as cetyl octanoate, lauryl lactate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;
g) essential oils such as fish oils, mentha, jasmine, camphor, white cedar, bitter orange peel, ryu, turpentine, cinnamon, beragmot, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, pinene, limonene and terpenoid oils;
h) lipids such as cholesterol, ceramides, sucrose esters and pseudo-ceramides as described in European Patent Specification No. 556 957;
i) vitamins such as vitamins A and E, and vitamin alkyl esters, including vitamin C alkyl esters;
j) sunscreens such as octyl methoxyl cinnamate (Parsol MCX) and butyl methoxy benzoylmethane (Parsol 1789);
k) Phospholipids; and
l) derivatives of alpha hydroxy acids such as materials of formula

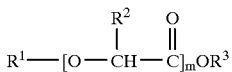

wherein $R^1$ is $C_pH_qN_rO_s$, where P is 0–20, q is 1–41, r is 0–3, and s is 0–3;

$R^2$ is $C_tH_u$ where t is 0–20 and u is 1–41;

$R^3$ is $C_vH_wN_xO_y$ where v is 0–20, w is 1–41, x is 0–3 and y is 0–3 or a metallic, ammonium or alkanolammonium anion; and m is 1–10;

m) perfumes;
n) germicides such as synthetic antimicrobials examples of which include salicylic acid; 1,6 bis (N-p-chlorphenyl biguanido) hexane (Chlorhexidine); chlorhexidine gluconate; 2,4,4 trichloro 2 hydroxy diphenyl ether (Irgosan DP300); imidazolidinyl urea; methyl, propyl, butyl, heptyl and benzyl p-hydroxy benzoate; 2 bromo-2-nitropropane 1,3 diol; nonyl phenol ethoxylate iodine complex; 2 phenoxy ethanol; 3-dimethylol-5, 5-dimethyl hydantoin; and natural antimicrobials examples of which include willow extract, neem tree extract; bamboo extract; and grapefruit extract;
o) mixtures of any of the foregoing components.

The invention has found particular application in the deposition of sunscreen agents e.g. UV absorbers and after-sun treatment materials; alkyl lactates, believed to penetrate the stratum corneum and release natural moisturisers; esters such as isopropyl palmitate; perfumes; vitamins; higher fatty acids such as linoleic acid; and mixtures thereof.

Suitable sunscreen include benzophenone compounds and derivatives of dibenzoyl methane, camphor and cinnamate and specifically Parsol MCX (2-ethyl hexyl methoxy cinnamate).

Alkyl lactates are materials having the formula

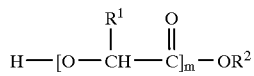

wherein $R^1$ is $C_xH_y$ where x and y are respectively numbers in the range 0 to 22 and 1 to 45; and R2 is $C_{x'}H_{y'}$ where x' and y' are respectively numbers in the range 1 to 22 and 3 to 45; and m is 1 to 10.

Particularly preferred materials include Crodamol LL (ex Croda), a lauryl lactate, or myristyl lactate.

Vitamins and derivatives thereof suitable for use in the present invention include vitamin C palmitate, vitamin E acetate and vitamin A palmitate.

It is an essential feature of the invention that the cosmetic benefit agent is substantially insoluble in the carrier by which is meant a proportion greater than 60% of the cosmetic benefit agent remains unpartitioned in the carrier at a temperature within the range 0–45° C. once the product has reached equilibrium.

The cosmetic benefit agent is preferably present in an amount from 0.1 to 10 wt %, most preferably 0.5 to 5wt %, based on the composition.

The Carrier

It is an essential feature of the present invention that the carrier material is substantially insoluble in the surfactant in the composition. By substantially insoluble is meant that it remains as stable suspended droplets thereby protecting the cosmetic benefit agent such that less than 10% is partitioned into the surfactant phase at a temperature within the range 0–45° C. once the product has reached equilibrium.

The carrier is preferably present in an amount from 0.48 to 49.8 wt % based on the composition.

Suitable carriers include silicone oils, gums and modifications thereof such as linear and cyclic polydimethylsiloxanes; amino, alkyl, alkylaryl and aryl silicone oils; fats and oils including natural fats and oils such as jojoba, soyabean, rice bran, avocado, almond, olive, sesame, persic, castor, coconut, mink oils; cacao fat, beef tallow, lard; hardened oils obtained by hydrogenating the aforementioned oils; and synthetic mono, di and triglycerides such as myristic acid glyceride and 2-ethylhexanoic acid glyceride; hydrocarbons such as liquid paraffins, petrolatum, microcrystalline wax, ceresin, and mineral oil in which the cosmetic benefit agent to be used is substantially insoluble. Particularly preferred are petrolatum; and polydimethyl siloxanes with a viscosity in the range of 200 to 500,000 cS at 25° C.

The Emulsifier

In the composition of the invention the emulsifier emulsifies the cosmetic benefit agent to form an internal phase of the second emulsion Preferably the emulsifier is present in amount from 0.1 to 5wt % based on the composition.

To form a stable emulsion the emulsifier should form a continuous monolayer between the carrier and the benefit agent. The emulsifier should be made up of a molecular complex of two materials. The first is substantially miscible with the benefit agent and the second is substantially miscible with the carrier phase.

Where the carrier phase is silicone oil or a derivative thereof, suitable emulsifiers include pendant substituted polydimethyl siloxanes and, particularly, materials substituted with pendant alkyl, phenyl, alkene groups and ethoxylated alkyl, amino, aryl or alkylaryl groups. When alkyl pendant substituted polydimethyl siloxanes are used the alkyl chain length is preferably in the range 12 to 30 and the materials contain a degree of substitution between 1 and 40%.

Suitable materials are those available from Dow Corning under the X2 series and include X2 5504, a lauryl material with between 10–40% Substitution; General Electric under the tradenames SF 160-D1 and SF 1632-D2, both substantially $C_{16}$ materials with 20% substitution; Goldschmidt under the tradename Abil Wax and Rhone Poulenc under the tradename Silbione, a series of $C_{22}$, $C_{18}$ or a $C_{22}/C_{18}$ material all with a degree of substitution of 33%.

Where the carrier phase is made up of a hydrocarbon oil a suitable emulsifier would be a molecular complex of a two components having polarities equivalent to the carrier and the benefit agent respectively.

The optimum choice of emulsifier is dependent on the cosmetic benefit agent being used and the carrier employed.

For example, when the cosmetic benefit agent is an alkyl lactate and the carrier is a polydimethylsiloxane the preferred emulsifier is one in which the alkyl substituent of the alkyl silicone matches the hydrocarbon chain length of the alkyl lactate.

The second emulsion is preferably present in an amount from 0.5 to 5wt % based on the total composition.

The Surfactant

A composition in accordance with the present invention also comprises at least one surfactant as an essential component, preferably in an amount of 1 to 35 wt %, most preferably 3 to 30 wt %.

The surfactant can be selected from any known surfactant suitable for topical application to the human body and is agent selected from anionic, nonionic, zwitterionic and cationic surfactants, soap and mixtures thereof. Mild surfactants, ie. surfactants which do not damage the stratum corneum, the outer layer of skin, are particularly preferred.

One preferred anionic detergent is a fatty acyl isethionate of formula:

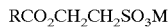

where R is an alkyl or alkenyl group of 7 to 21 carbon atoms and M is a solubilising cation such as sodium, potassium, ammonium or substituted ammonium. Preferably at least three quarters of the RCO groups have 12 to 18 carbon atoms and may be derived from coconut, palm or a coconut/palm blend.

Another preferred anionic detergent is alkyl ether sulphate of formula:

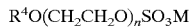

where $R^4$ is an alkyl group of 8 to 22 carbon atoms, n ranges from 0.5 to 10 especially 1.5 to 8, and M is a solubilising cation as before.

Other possible anionic detergents include alkyl glyceryl ether sulphate, sulphosuccinates, taurates, sarcosinates, sulphoacetates, alkyl phosphate, alkyl phosphate esters and acyl lactylate, alkyl glutamates and mixtures thereof.

Sulphosuccinates may be monoalkyl sulphosuccinates having the formula:

and amido-MEA sulphosuccinates of the formula:

wherein $R^5$ ranges from $C_8$–$C_{20}$ alkyl, preferably $C_{12}$–$C_{15}$ alkyl and M is a solubilising cation.

Sarcosinates are generally indicated by the formula:

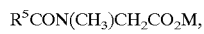

wherein $R^5$ ranges from $C_8$–$C_{20}$ alkyl, preferably $C_{12}$–$C_{15}$ alkyl and M is a solubilising cation.

Taurates are generally identified by the formula:

wherein $R^5$ ranges from C8–$C_{20}$ alkyl, preferably $C_{12}$–$C_{15}$ alkyl, $R^6$ ranges from $C_1$–$C_4$ alkyl, and M is a solubilising cation.

Harsh surfactants such as primary alkane sulphonate or alkyl benzene sulphonate will generally be avoided.

Suitable nonionic surface active agents include alkyl polysaccharides, lactobionamides, ethyleneglycol esters, glycerol monoethers, polyhydroxyamides (glucamide), primary and secondary alcohol ethoxylates, especially the $C_{8-20}$ aliphatic alcohols ethoxylated with an average of from 1 to 20 moles of ethylene oxide per mole of alcohol.

If the surface active agent comprises soap, the soap is preferably derived from materials with a $C_8$ to $C_{22}$, substantially saturated, carbon chain and, preferably, is a potassium soap with a $C_{12}$ to $C_{18}$ carbon chain.

Mixtures of any of the foregoing surface active agents may also be used.

It is also preferable that the composition includes from 0.5 to 15 wt % of a cosurfactant agent with skin-mildness benefits. Suitable materials are zwitterionic detergents which have an alkyl or alkenyl group of 7 to 18 carbon atoms and comply with an overall structural formula

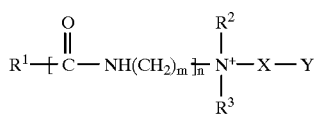

where $R^1$ is alkyl or alkenyl of 7 to 18 carbon atoms $R^2$ and $R^3$ are each independently alkyl, hydroxyalkyl or carboxyalkyl of 1 to 3 carbon atoms m is 2 to 4 n is 0 or 1

X is alkylene of 1 to 3 carbon atoms optionally substituted with hydroxyl, and

Y is $-CO_2^-$ or $-SO_3^-$

Zwitterionic detergents within the above general formula include simple betaines of formula:

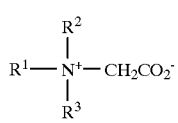

and amido betaines of formula:

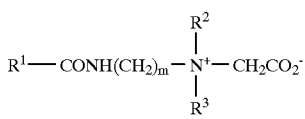

where m is 2 or 3.

In both formulae $R^1$, $R^2$ and $R^3$ are as defined previously. $R^1$ may, in particular, be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is a sulphobetaine of formula:

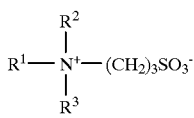

or

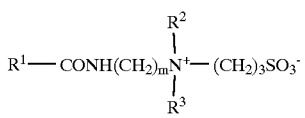

where m is 2 or 3, or variants of these in which $—(CH_2)_3SO_3^-$ is replaced by

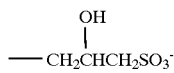

$R^1$, $R^2$ and $R^3$ in these formulae are as defined previously.

Although the compositions of the invention may be self-structuring generally they will comprise a structurant and/or a thickener. Suitable materials include swelling clays, for example laponite; fatty acids and derivatives thereof and, in particular, fatty acid monoglyceride polyglycol ethers; cross-linked polyacrylates such as Carbopol (TM) (polymers available from Goodrich); acrylates and copolymers thereof, polyvinylpyrrolidone and copolymers thereof; polyethylene imines; natural gums including alginates, guar, xanthan and polysaccharide derivatives including carboxy methyl cellulose and hydroxypropyl guar; propylene glycols and propylene glycol oleates; salts such as sodium chloride and ammonium sulphate; sucrose esters; gellants; and mixtures thereof.

Of the clays, particularly preferred are synthetic hectorite (laponite) clay used in conjunction with an electrolyte salt capable of causing the clay to thicken. Suitable electrolytes include alkali and alkaline earth salts such as halides, ammonium salts and sulphates; and mixtures thereof.

Further examples of structurants and thickeners are given in the International Cosmetic Ingredient Dictionary, Fifth Edition, 1993, published by CTFA (The Cosmetic, Toiletry & Fragrance Association), incorporated herein by reference. Deposition aids, in particular cationic polymers such as cationic derivatives of guar gum and quaternary nitrogen-substituted cellulose ether derivatives may be added to the cosmetic composition to further enhance deposition of the cosmetic agent. Suitable cationic guar gum derivatives are those given the CTFA designation guar hydroxylpropyl trimonium chloride, available commercially for example as Jaguar C13S, which has a low degree of substitution of cationic groups and a high viscosity. Other suitable materials include Jaguar C15 and Jaguar C16. Suitable quaternary nitrogen substituted cellulose ether derivatives include those available commercially as the Polymer JR series. Such materials, if present, are added in an amount of 0.01 to 10 wt % based on the composition.

Examples of other adjuncts which may be added to the composition of the invention include opacifiers; preservatives such as para-hydroxy benzoate esters; antimicrobials, antioxidants such as butyl hydroxy toluene; bactericides; humectants such as glycerol and sorbitol; plant extracts such as Aloe Vera, witch hazel and elderflower; colourants; and perfumes.

Compositions of the invention may be formulated for washing the skin and hair, for example, bath or shower gels; handwashing compositions; facial washing compositions; and pre- and post-shaving products.

The compositions of the invention will generally be pourable liquids or semi-liquids, for example, pastes and will, preferably, have a viscosity in the range 1000 to 100,000 mpas measured at a shear rate of $10s^{-1}$ and 25° C. in a Haake Rotoviscometer RV20.

According to a further aspect of the invention there is provided a process for preparing a rinse-off cleansing composition according to claim 1 comprises:

i) emulsifying the cosmetic benefit agent with an emulsifier in a carrier to form a second emulsion;

ii) adding the second emulsion to the at least one surfactant to form a first emulsion; and iii) adding any optional components to the first emulsion.

The invention is further illustrated by the following non-limiting examples.

EXAMPLES

In the examples:

APG (Alkylpolyglucoside) was Plantaren 2000 ex Henkel. Behenyl alcohol was Nacol 22-97 ex Condea. Behenyl PDMS was Silbione 71649 ex Rhone Poulenc. Coco amidopropyl betaine was Amonyl BA 380 ex Seppic. Cross-linked polyacrylate was Carbopol ETD 2020 ex Goodrich. DC556 is polyphenyldimethyl siloxane ex Dow Corning IPP (isopropyl palmitate) was Estol 1517 ex Unichema. Lauryl lactate was Crodamol LL ex Croda Chemicals. MEA sulphosuccinate was Witco 5690 Ex Witco. PDMS was polydimethylsiloxane of varying viscosities ex Dow Corning. SF1265 was phenyl silicone ex General Electric Sodium cocoyl isethionate was Jordapon SCI ex PPG/Mazer. Sodium lauryl ether sulphate was Genapol ZRO ex Hoechst. Stearyl PDMS was X25502 ex Dow Corning. Stearic acid was Pristerine 4911 ex Unichema. Sunscreen was 2 ethyl hexyl methoxy cinnamate (Parsol MCX), ex Givaudan Co Ltd. Thickener was Antil 141 (a propylene glycol and propylene glycol oleate) ex Goldschmidt.

Examples 1–4

The following method was used to determine the amount of sunscreen deposited onto full thickness porcine skin (5×5 cm) treated with compositions according to the invention.

The skin was prehydrated and then 0.16 ml of the product applied to it. The product was lathered for 10 seconds and then rinsed for 10 seconds under running water.

Thereafter the skin was wiped once with a paper towel to remove excess water.

Two minutes after drying the deposited sunscreen was extracted from the skin using ethanol three times (3 ml per extract). The extracts were combined and made up to 10 g using ethanol.

The level of sunscreen was determined using a UV/visible spectrophotometer and comparing the absorbance with a standard calibration curve.

Three pieces of skin were used per tested product.

The following method was used to determine the amount of silicone oil deposited onto full thickness porcine skin (5×15 cm) treated with compositions according to the invention.

The skin was prehydrated and then 0.5 ml of the product applied to it. The product was lathered for 10 seconds and then rinsed for 10 seconds under running water.

Thereafter the skin was wiped once with a paper towel to remove excess water.

2 minutes after drying a strip of adhesive tape was pressed onto the skin for 60 seconds by applying a constant load of 100 g.cm$^{-2}$. The adhesive tape employed was J-Lar Superclear (TM) tape having a width of 2.5 cm. In total five strips of tape were applied to adjacent sites on each piece of skin. Two pieces of skin were used for testing each product.

In this test procedure silicone which has deposited on the skin will subsequently be transferred to the tape along with some of the outer layer of the skin.

The amounts of silicone and skin adhering to the tape are determined by means of X-ray fluorescence spectroscopy. The tape strips are placed in an X-ray fluorescence spectrometer with the adhesive side facing the beam of this machine. A mask is applied over the tape to define a standardised area in the middle of the tape which is exposed to the X-ray beam. The sample chamber of the machine is placed under vacuum before making measurements and the spectrometer is then used to measure the quantities of silicon and sulphur. The sulphur is representative of the amount of skin which has transferred to the tape.

The amounts of silicon and sulphur observed with a clean piece of adhesive tape are subtracted from the experimental measurements. The experimental measurements for the average levels of sulphur and silicon are expressed as a ratio of silicon to sulphur. From this ratio it is possible to determine silicone oil deposition per unit area of skin.

Example 1

A base facial wash product having the following composition was prepared.

|  | Wt % |
|---|---|
| Sodium lauryl ether sulphate (SLES) | 4.00 |
| Coco amidopropyl betaine (CAPB) | 1.00 |
| Alkyl polyglucoside (APG) | 5.00 |
| Sorbic Acid | 0.37 |
| Sodium citrate dihydrate | 0.49 |
| Thickener | 0.97 |
| pH adjustor | ~1.00 |
| minors & water | to 100 |

The formulation was prepared by mixing the APG, SLES and CAPB with excess water. Thereafter the preservative was added. The pH and viscosity of the resulting composition was adjusted to give a composition with a pH of 5.3 and viscosity of 5500 mPas at 25° C. at 10s$^{-1}$.

An emulsion of formula

|  | % wt |
|---|---|
| Sunscreen | 10 |
| Emulsifier either Behenyl or Stearyl PDMS | 10 |
| PDMS 60000 cS | 80 | was also prepared using two different emulsifiers and silicone oils of different viscosities. The emulsion was prepared by mixing the emulsifier and sunscreen together in a glass vessel. When a highly substituted behenyl polydimethyl siloxane was the chosen emulsifier a mixture of the emulsifier and sunscreen were heated to 60° C. to melt the former into the latter.

Thereafter, the silicone oil was added slowly to the emulsified sunscreen whilst shearing on a Silverson high shear mixer. The resulting product was then hand mixed into the base formulation to produce a product with large droplets of emulsion in which the sunscreen was present at a level of 2%.

The amount of silicone oil and sunscreen deposited onto skin treated with compositions according to the invention was determined as described above.

Comparisons were carried out with
i) a base formulation incorporating the same amount of silicone oil (PDMS) as the examples according to the invention but in the absence of emulsified cosmetic benefit agent; and
ii) a base formulation incorporating 2% sunscreen.

The following results demonstrate the improved deposition of sunscreen from the compositions according to the invention.

| Example | Silicone Oil | Emulsifier | Cosmetic Benefit Agent | Si:S | Sunscreen Deposition (ppm) |
|---|---|---|---|---|---|
| 1 | PDMS (60000 cS) | Behenyl PDMS | Sunscreen | 156 | 48.9 |
| 2 | PDMS (60000 cS) | Stearyl PDMS | Sunscreen | 31.9 | 23.4 |
| A | PDMS (60000 cS) | — | — | 10.7 | — |
| B | — | — | Sunscreen | — | 5.0 |
| 3 | PDMS (5000 cS) | Behenyl PDMS | Sunscreen | 66.9 | 24.6 |
| 4 | PDMS (5000 cS) | Stearyl PDMS | Sunscreen | 17.6 | 15.6 |
| C | PDMS (5000 cS) | — | — | 6.4 | — |

Examples 5–9

In this series of examples deposition of IPP (isopropyl palmitate) from compositions in accordance with the invention was investigated.

The following method was used to determine the amount of IPP deposited onto full thickness porcine skin (5×15 cm pieces) treated with compositions according to the invention.

The skin was prehydrated and then 0.5 ml of the product applied to it. The product was lathered for 10 seconds and then rinsed for 10 seconds under running water.

Thereafter the skin was wiped once with a paper towel to remove excess water.

After drying for 2 minutes, the skin was extracted with ethanol three times (3 ml per extract), the extract made up to 10 g and submitted for Gas Chromatography analysis to determine the amount of IPP deposited.

The base formulation used in this example was the same as that used in examples 1 to 4.

An emulsion of formula:

|  | % wt |
| --- | --- |
| IPP | 45 |
| Behenyl PDMS | 5 |
| Silicone Oil | 50 | was prepared using a range of silicone oils varying in viscosity. The emulsion was prepared by melting the Behenyl PDMS and IPP together in a glass vessel. Thereafter the silicone oil was added slowly to the emulsified IPP whilst shearing on a Silverson high shear mixer. The resulting product was then hand mixed into the base formulation to produce a product in which IPP was present at a level of 4.5% wt based on the total formulation.

The amount of IPP deposited onto skin treated with compositions according to the invention was determined as described above. The following results were obtained and demonstrate the advantage of the invention over a system in which emulsified IPP is incorporated directly into a base surfactant composition in the absence of a silicone oil carrier.

|  | Silicone Oil | Deposition/ppm |
| --- | --- | --- |
| 5 | PDMS (5000 cS) | 12 |
| 6 | PDMS (12500 cS) | 17 |
| 7 | PDMS (30000 cS) | 15 |
| 8 | PDMS (60000 cS) | 23 |
| D | No silicone oil | 0.7 |

Examples 9–12

The following method was used to determine the amount of lauryl lactate deposited onto full thickness porcine skin (5×15 cm) treated with compositions according to the invention containing lauryl lactate (examples 9–12) and comparative systems (examples E–H).

The skin was prehydrated and then 0.20 g of the product and 0.1 g of water applied to it. The skin was washed for 30 seconds and then rinsed for 15 seconds under running water.

Thereafter the skin was wiped once with a paper towel to remove excess water.

30 minutes after drying, the skin was tape stripped by pressing a strip of adhesive tape onto the skin for 30 seconds by applying a constant load of 100 g cm$^{-2}$.

In total five strips of Desquame tape (Diastron) were applied to the centre area of the skin and two strips of J-LAR (Permacel) were applied to the sides of the skin sample.

The Desquame strips were then removed from the skin and hydrolysed in 2 ml of NaOH (0.5M) at 60° C. for 60 minutes. They were then neutralised with 2 ml HCl (0.5M) and in Sorensens phosphate buffer (pH 7.0). The total lauryl lactate and the protein content of the tapes, representative of the lauryl lactate transferred to the skin, was determined using Sigma diagnostic assay Kits 735/10 and 690. A solution containing the assay and treated strips was prepared and the absorbance at 540 nm measured in a uv spectrometer.

The J-LAR tapes were analysed for silicone using XRF as described above.

The formulation of the final product was

|  | Wt % |
| --- | --- |
| Sodium cocoyl isethionate | 8.9 |
| MEA sulphosuccinate | 11.7 |
| Coco amidopropyl betaine | 12.5 |
| Cross-linked polyacrylate | 0.4 |
| Behenyl alcohol | 3.00 |
| Stearic acid | 3.00 |
| Glycerol | 8.00 |
| Thickener | 0.50 |
| Emulsion | 16 |
| Water and minors | to 100% |

The emulsion comprised

|  | % wt |
| --- | --- |
| Silicone Oil | 10 |
| Lauryl lactate | 5 |
| Emulsifier | 1 |

The product was prepared as follows:

The surfactants were hydrated in a first vessel in 20% water and to this was added glycerol. The resulting mixture was added to the cross-linked polyacrylate and heated to 50° C. whilst stirring. The fatty acid and behenyl alcohol were then added.

In a second vessel the emulsifier was blended into the lauryl lactate at 50° C. and PDMS added slowly using a high shear mixer until a smooth cream was formed.

The first vessel was cooled to room temperature and thereafter the mixer was set at a high speed and the emulsion added. The speed of the mixer was reduced and the pH of the resulting mixture adjusted to pH 6.75 using 20% NaOH. Thereafter optional components such as preservatives were added and the thickener added to give a product with a required thickness.

The stability of products were assessed for four weeks at 37° C. and twelve weeks at room temperature. The most stable formulations were found when the product
i) contained a structurant such as cross linked polyacrylate or a clay such as Laponite;
ii) when the emulsifier was behenyl PMDS. It is believed this emulsifier has the added benefit of thickening the internal phase of the emulsion, thus preventing the droplets coalescing.

The following deposition results were obtained:

| Example | Formulation | Lactate/Absorbance Units | Si:S |
| --- | --- | --- | --- |
| 9 | 16% emulsion Lauryl lactate Lauryl PDMS PDMS (5000 cS) | 0.164 | 5.27 |
| 10 | 16% emulsion Lauryl lactate Lauryl PDMS PDMS (60000 cS) | 0.164 | 5.12 |
| 11 | 16% emulsion Lauryl lactate Behenyl PDMS PDMS (5000 cS) | 0.173 | 6.08 |
| 12 | 16% emulsion Lauryl lactate Behenyl PDMS PDMS (60000 cS) | 0.157 | 6.04 |

-continued

| Example | Formulation | Lactate/Absorbance Units | Si:S |
|---|---|---|---|
| E | Formulation without emulsion | 0.116 | 0.052 |
| F | 5% Lauryl lactate added to formulation no emulsion | 0.136 | 0.17 |
| G | 5% PDMS (60000 cS) added to formulation no emulsion | 0.108 | 3.21 |
| H | water only | 0.119 | 0.010 |

(The balance of the formulations of examples E, F, and G were made up with water.)

The results demonstrate the advantage of the compositions according to the invention in terms of the amount of lactate deposited.

Example 13

In this set of experiments deposition of lauryl lactate from a large droplet silicon emulsion with a mean droplet size of greater than 50 μm was determined.

The same method as described in examples 9 to 11 was used to determine the amount of lauryl lactate deposited onto treated skin.

The base formulation for the following experiments was:

|  | Wt % |
|---|---|
| MEA Sulphosuccinate | 11.7 |
| Cross-linked polyacrylate | 0.3 |
| Sodium cocoyl isethionate | 8.5 |
| Coco amidopropyl betaine | 15.8 |
| Water and minors | to 100 |

It was prepared by dispersing the polyacrylate in excess water. A premix of the two surfactants was then added to the polymer dispersion. Thereafter minors were added.

The following emulsions was prepared by the method described above.

|  | % wt |
|---|---|
| Lauryl lactate | 27.03 |
| Behenyl PDMS | 18.92 |
| PDMS (5000 cS) | 54.05 |

The following results were obtained which demonstrate the advantage of the composition according to the invention.

|  | Lactate/Absorbance Units |
|---|---|
| Base & 5% emulsion | 0.164 |
| Base formulation | 0.063 |
| Base & 5% Lauryl lactate | 0.102 |

Example 14

This example demonstrate the advantage of the compositions of the present invention over a system in which the cosmetic benefit agent is dissolved in an oil phase and the resulting product emulsified by a surfactant.

A base formulation having the following composition was prepared.

|  | Wt % |
|---|---|
| Sodium lauryl ether sulphate (SLES) | 8.00 |
| Coco amidopropyl betaine (CAPB) | 2.00 |
| Cross-linked polyacrylate | 0.9 |
| pH adjustor | ~5.3 |
| minors & water | to 100 |

The formulation was prepared by adding the polyacrylate to water and allowing it to hydrate. The SLES and CAPB were mixed and then added to the polyacrylate dispersion. The pH of the formulation was adjusted using 5N sodium hydroxide.

We claim:

1. A rinse-off cleansing composition including at least one surfactant soluble cosmetic benefit agent and at least one surfactant, the composition comprising:
    (a) an external phase comprising a first emulsion having a continuous phase comprising at least one surfactant present In an amount of about 1% to 35% by wt. of the composition; and
    (b) an internal phase comprising about 0.5% to 50% by wt. of total composition which comprises a second emulsion and wherein said second emulsion comprises:
        (i) a continuous phase comprising about 0.48% to 49.8% by wt. total composition of a carrier in which about 0.1 to 10% by wt. total composition of said cosmetic benefit agent is substantially insoluble, said carrier being substantially surfactant insoluble; and
        (ii) an internal phase comprising said cosmetic benefit agent and about 0.1 to 5% by wt. total composition of an emulsifier for said benefit agent;
    wherein said cosmetic benefit agent is selected from the group consisting of waxes; hydrophobic plant extracts; hydrocarbons; higher fatty acids; higher fatty alcohols; esters; essential oils; lipids; phosphollpids; vitamins; sunscreens; derivatives of alpha hydroxy acids; perfumes; germicides and mixtures thereof;
    wherein said emulsifier is a pendant, substituted polydimethyl siloxane; and
    wherein said carrier is selected from the group consisting of silicone oils; gums; fats and oils; synthetic mono, di and triglycerides; liquid paraffins; petrolatum; microcrystalline wax; ceresin; and mineral oil in which the cosmetic benefit agent is substantially insolubler.

2. A composition according to claim 1 wherein the second emulsion comprises a continuous phase comprising petrolatum and an internal phase comprising a cosmetic benefit agent selected from the group consisting of alkyl lactates; sunscreen; esters; perfumes; higher fatty acids; and vitamins emulsified by a hydrocarbon emulsifier.

3. A composition according to claim 1 wherein the second emulsion comprises a continuous phase comprising polydimethyl siloxane and an internal phase comprising a cosmetic benefit agent selected from the group consisting of alkyl lactates; sunscreens; esters; perfumes; higher fatty acids; and vitamins emulsified by a pendant alkyl substituted polydimethyl siloxane.

4. A process for preparing a rinse-off cleansing composition according to claim 1 comprising:
    i) emulsifying the cosmetic benefit agent with an emulsifier in a carrier to form a second emulsion;
    ii) adding the second emulsion to a mixture of the at least one surfactant to form a first emulsion; and
    iii) adding any optional components to the first emulsion.

* * * * *